(12) United States Patent
Stephens, Jr. et al.

(10) Patent No.: US 9,814,234 B2
(45) Date of Patent: Nov. 14, 2017

(54) BIOACTIVE HEME-HALOPEROXIDASE COMPOSITIONS AND METHODS OF THEIR USE

(71) Applicant: Exoxemis, Inc., Little Rock, AR (US)

(72) Inventors: Jackson T. Stephens, Jr., Little Rock, AR (US); Matthew J. Pete, Lebanon, OH (US)

(73) Assignee: EXOXEMIS, INC., Little Rock, AR (US)

( * ) Notice: Subject to any disclaimer, the term of this patent is extended or adjusted under 35 U.S.C. 154(b) by 47 days.

(21) Appl. No.: 14/593,648

(22) Filed: Jan. 9, 2015

(65) Prior Publication Data

US 2015/0196025 A1 Jul. 16, 2015

Related U.S. Application Data

(60) Provisional application No. 61/927,406, filed on Jan. 14, 2014.

(51) Int. Cl.
| | | |
|---|---|---|
| *A61K 38/54* | (2006.01) | |
| *A01N 33/08* | (2006.01) | |
| *A61K 38/44* | (2006.01) | |
| *A61K 31/133* | (2006.01) | |
| *A61K 33/40* | (2006.01) | |
| *A61K 45/06* | (2006.01) | |
| *A61K 33/00* | (2006.01) | |

(52) U.S. Cl.
CPC ............ *A01N 33/08* (2013.01); *A61K 31/133* (2013.01); *A61K 33/00* (2013.01); *A61K 33/40* (2013.01); *A61K 38/44* (2013.01); *A61K 38/443* (2013.01); *A61K 45/06* (2013.01); *C12Y 101/03004* (2013.01); *C12Y 111/01007* (2013.01)

(58) Field of Classification Search
CPC ...... A61K 33/40; A61K 45/06; A61K 38/443; A61K 33/00; A61K 31/133; A61K 2300/00; C12Y 111/01007; A01N 33/08; A01N 37/46
See application file for complete search history.

(56) References Cited

U.S. PATENT DOCUMENTS

| | | |
|---|---|---|
| 5,389,369 A | 2/1995 | Allen |
| 5,451,402 A | 9/1995 | Allen |
| 5,510,104 A | 4/1996 | Allen |
| 6,251,386 B1 | 6/2001 | Johansen |
| 6,294,168 B1 | 9/2001 | Allen |
| 6,855,328 B2 | 2/2005 | Hei et al. |
| 8,945,540 B2 | 2/2015 | Becquerelle et al. |
| 2001/0009664 A1 | 7/2001 | Johansen |
| 2007/0045199 A1* | 3/2007 | Mayer .............. A01N 59/00 210/764 |
| 2008/0114054 A1 | 5/2008 | Microbes et al. |

FOREIGN PATENT DOCUMENTS

| | | |
|---|---|---|
| WO | 0247483 A1 | 6/2002 |
| WO | 2013009910 A3 | 6/2013 |

OTHER PUBLICATIONS

Anderson, M.M., et al., "The Myeloperoxidase System of Human Phagocytes Generates N?-(carboxymethyl)lysine on Proteins: a Mechanism for Producing Advanced Glycation End Prodicts at Sites of Inflammation," The Journal of Clinical Investigation 104(1):103-113, Jul. 1999.
International Search Report, PCT/US2015/011435, dated Apr. 7, 2015, 5 Pgs.

* cited by examiner

*Primary Examiner* — Satyendra K Singh
(74) *Attorney, Agent, or Firm* — K&L Gates LLP

(57) ABSTRACT

Compositions comprising a heme-haloperoxidase and an amino alcohol effective for killing or inhibiting the growth of pathogenic microorganisms in the presence of a peroxide and halide and methods of use are provided.

33 Claims, 6 Drawing Sheets

Figure 1:
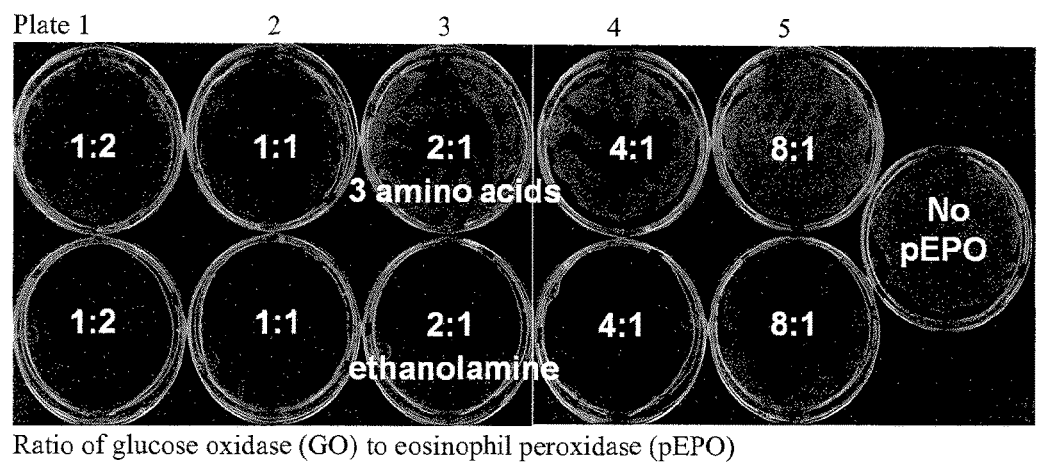
Figure 2:
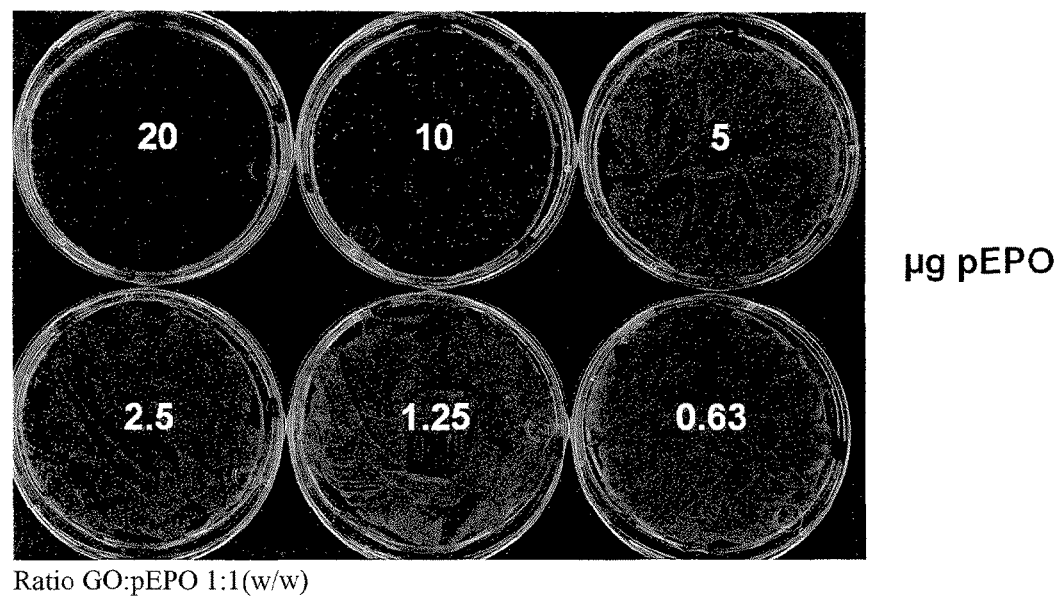
Figure 3:
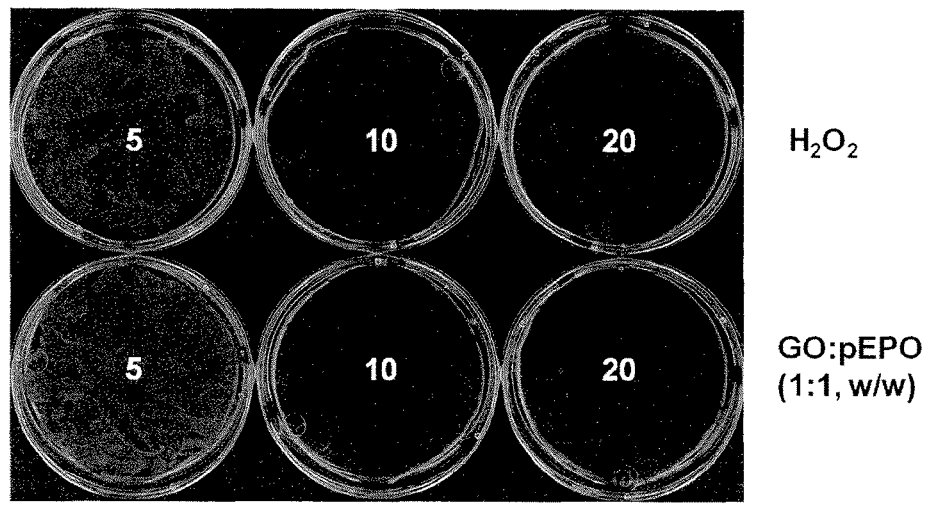
Figure 4:
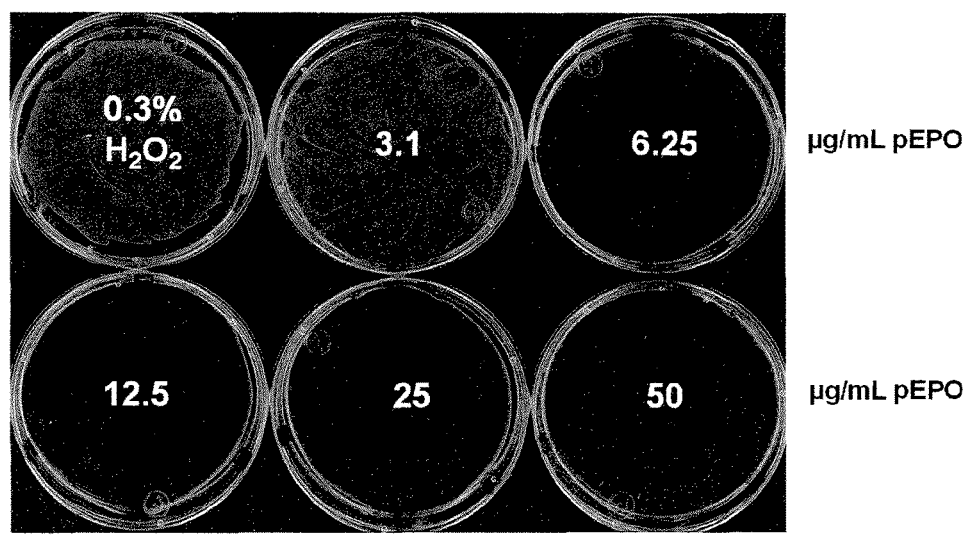
Figure 5:
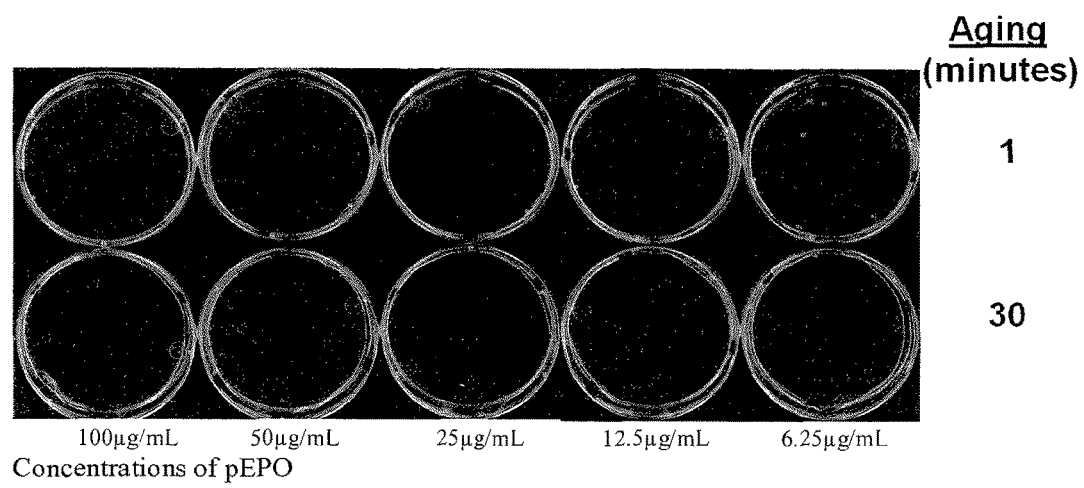
Figure 6:
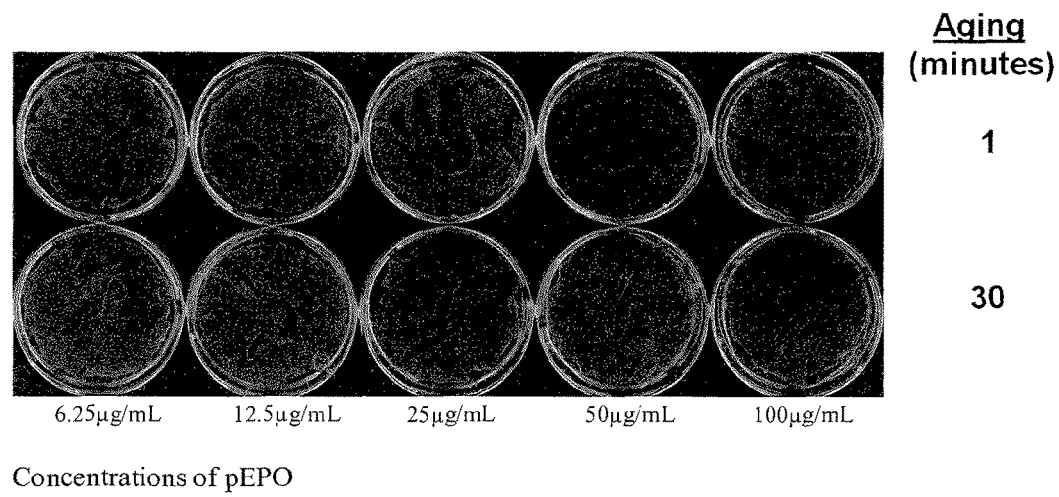
Figure 7:
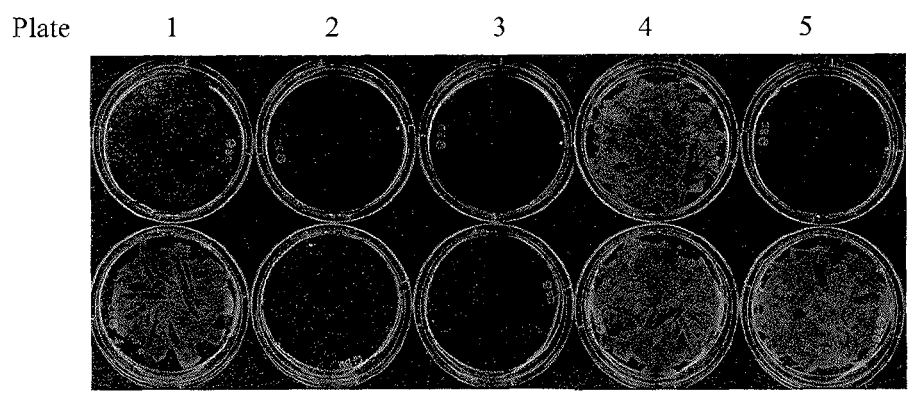
Figure 8A:
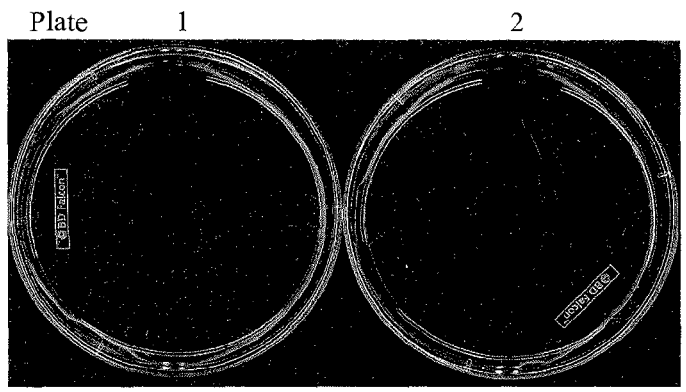
Figure 8B:
Figure 8C:
Figure 9A:
Figure 9B:

Ratio of glucose oxidase (GO) to eosinophil peroxidase (pEPO)

Ratio GO:pEPO 1:1(w/w)

Plate  1  2  3  4  5

Plate    1            2            3

Plate    1            2            3

BIOACTIVE HEME-HALOPEROXIDASE COMPOSITIONS AND METHODS OF THEIR USE

CROSS-REFERENCE TO RELATED APPLICATION

This application claims the benefit of U.S. Provisional Application No. 61/927,406 filed Jan. 14, 2014, incorporated by reference herein.

FIELD OF THE PRESENT DISCLOSURE

The present disclosure is directed to compositions comprising a heme-haloperoxidase and an amino alcohol effective for killing or inhibiting the growth of pathogenic microorganisms in the presence of a peroxide and halide and methods of use.

BACKGROUND

As disclosed in U.S. Pat. Nos. 5,888,505 and 6,294,168, haloperoxidases may be used to selectively bind to and, in the presence of peroxide and halide, inhibit the growth of target pathogenic microorganisms without eliminating desirable microorganisms or significantly damaging other components of the medium, such as host cells and normal flora, in the target microorganism's environment. Haloperoxidases have previously been known to exhibit microorganism killing activity in natural systems when presented with an appropriate halide cofactor ($X^-$) and hydrogen peroxide as substrate (Klebanoff, 1968, *J. Bacteria* 95:2131-2138). The selective nature of haloperoxidase binding and the utility of these compounds for therapeutic, research and industrial applications is known. Due to the selective binding properties of haloperoxidases, when a target microorganism, such as a pathogenic microorganism, has a binding capacity for haloperoxidase greater than that of a desired microorganism, such as members of the normal flora, the target microorganism selectively binds the haloperoxidase with little or no binding of the haloperoxidase by the desired microorganism. In the presence of peroxide and halide, the target bound haloperoxidase catalyzes halide oxidation and facilitates the disproportionation of peroxide to singlet molecular oxygen ($^1O_2$) at the surface of the target microorganism, resulting in selective killing of the target microorganism with a minimum of collateral damage to the desired microorganism or physiological medium. Thus, as disclosed in U.S. Pat. Nos. 5,888,505 and 6,294,168, haloperoxidases can be employed as an antiseptic in the therapeutic or prophylactic treatment of human or animal subjects to selectively bind to and kill pathogenic microorganisms with a minimum of collateral damage to host cells and normal flora of the host.

Haloperoxidases may also be employed as disinfecting or sterilizing formulations for inhibiting the growth of target microorganisms in vitro, particularly in applications where biomedical devices, such as bandages, surgical instruments, suturing devices, catheters, dental appliances, contact lenses and the like, are antiseptically treated to inhibit the growth of target microorganisms without damage to host cells of a subject when the biomedical device is subsequently utilized in vivo.

As disclosed in U.S. Pat. Nos. 5,389,369 and 5,451,402, while the haloperoxidase antiseptic system disclosed in U.S. Pat. Nos. 5,888,505 and 6,294,168 has been found to be highly effective in the treatment of pathogenic microbes, a microbicidal activity enhancing agent may be required for the effective killing of yeast and spore forming microorganisms. The spore stage of the microbial life cycle is characterized by metabolic dormancy and resistance to environmental factors that would destroy the microbe in its vegetative stage. The earliest phase of spore germination is characterized by swelling and a shift from dormancy to active metabolism. Vegetative growth, e.g., sprouting, and ultimately reproduction follows.

Germination of bacterial endospores and fungal spores is associated with increased metabolism and decreased resistance to heat and chemical reactants. For germination to occur, the spore must sense that the environment is adequate to support vegetation and reproduction. The amino acid L-alanine is reported to stimulate bacterial spore germination (Hills, 1950, *J Gen Microbiol* 4:38; Halvorson and Church, 1957, *Bacteriol Rev* 21:112). L-Alanine and L-proline have also been reported to initiate fungal spore germination (Yanagita, 1957, *Arch Mikrobiot* 26:329).

Simple α-amino acids, such as glycine and L-alanine, occupy a central position in metabolism. Transamination or deamination of α-amino acids yields the glycogenic or ketogenic carbohydrates and the nitrogen needed for metabolism and growth. For example, transamination or deamination of L-alanine yields pyruvate which is the end product of glycolytic metabolism (Embden-Meyerhof-Parnas Pathway). Oxidation of pyruvate by pyruvate dehydrogenase complex yields acetyl-CoA, NADH, $H^+$, and $CO_2$. Acetyl-CoA is the initiator substrate for the tricarboxylic acid cycle (Kreb's Cycle) which in turns feeds the mitochondrial electron transport chain. Acetyl-CoA is also the ultimate carbon source for fatty acid synthesis as well as for sterol synthesis. Simple α-amino acids can provide the nitrogen, $CO_2$, glycogenic and/or ketogenic equivalents required for germination and the metabolic activity that follows.

Accordingly, U.S. Pat. Nos. 5,389,369 and 5,451,402 disclose that the microbicidal action of haloperoxidases against yeast and sporular forms of microbes may be enhanced by treating the microorganisms with a haloperoxidase in combination with certain α-amino acids which provide a stimulating effect on yeast budding, germination of sporulated microbes, and possibly acceleration of metabolism of vegetative microbes. Representative α-amino acids disclosed for this purpose include glycine and the L- or D-enantiomers of alanine, valine, leucine, isoleueinc, serine, threonine, lysine, phenylalanine, tyrosine, and the alkyl esters thereof. While U.S. Pat. Nos. 5,389,369 and 5,451,402 disclose the enhancement of microbicidal activity of haloperoxidase against yeast and sporular forms of microbes with α-amino acids, these patents do not disclose enhancement of the haloperoxidase microbicidal system against non-sporular bacteria.

U.S. Patent Application Publication No. 20090280102 describes enhancement of a haloperoxidase, myeloperoxidase, microbicidal system against bacteria by combining myeloperoxidase with at least two amino acids. U.S. Patent Application Publication No. 20140120076 describes enhancement of a haloperoxidase, eosinophil peroxidase, microbicidal system against bacteria by combining eosinophil peroxidase with at least two amino acids.

The applicants of the present disclosure have found that the antibacterial activity of haloperoxidases can be enhanced by the presence of amino alcohols, e.g. ethanolamine, diethanolamine, or propanolamine. Accordingly, the present disclosure is directed to compositions comprising a haloperoxidase and an amino alcohol, e.g. ethanolamine, diethanolamine, or propanolamine, and methods of their use, as disclosed herein.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, the present disclosure is directed to compositions for killing or inhibiting the growth of pathogenic microorganisms in the presence of a peroxide and a halide, the compositions comprising a hence-haloperoxidase, e.g. eosinophil peroxidase, and ethanolamine, diethanolamine, or propanolamine.

In one aspect, the present disclosure is directed to methods of using compositions comprising a heme-haloperoxidase, e.g. eosinophil peroxidase, and ethanolamine, diethanolamine, or propanolamine for killing or inhibiting the growth of pathogenic microorganisms in the presence of a peroxide and a halide.

DETAILED DESCRIPTION

The present disclosure is directed to compositions and methods for killing pathogenic bacteria or inhibiting bacterial infections in the presence of peroxide and halide, the compositions comprising a heme-haloperoxidase and an amino alcohol having the formula $NH_2CH_2CH_2OH$ (referred to herein as "ethanolamine"), $HN(CH_2CH_2OH)_2$ (referred to herein as "diethanolamine"), or $NH_2CH_2CH_2CH_2OH$ (referred to herein as "propanolamine"). As used herein, the term "heme-haloperoxidase" refers to a mammalian haloperoxidase that contains a heme-prosthetic group. Heme-haloperoxidases are halide:hydrogen peroxide oxidoreductases for which halide (i.e., chloride, bromide, or iodide) or pseudo-halide (e.g., thiocyanate), is the electron donor or reductant and peroxide is the electron receiver or oxidant. Heme-haloperoxidases useful in the compositions and methods of the present disclosure include eosinophil peroxidase, myeloperoxidase, and lactoperoxidase.

In one aspect of the present disclosure, compositions for inhibiting the growth of, or killing, a pathogenic microorganism is provided. Representative pathogenic microorganisms may include, but are not limited to, both Gram-positive and Gram-negative organisms, such as, for example, *Enterococcus faecalis, Enterococcus faecium, Staphylococcus aureus, Staphylococcus epidermidis, Streptococcus agalactiae, Streptococcus* Group C, *Streptococcus* Group F, *Streptococcus* Group G, *Streptococcus pyogenes, Citrobacter freundii, Enterobacter cloacae, Escherichia coli, Klebsiella pneumoniae, Proteus Acintobacter* spp., *Pseudomonas aeruginosa, Aeromonas hydrophilia,* and *Pasteurella multocida*. In addition, the compositions of the present disclosure may be useful in inhibiting the growth of, or killing, spore forming microorganisms such as, for example, bacteria such as *Bacillus* sps. and *Clostridium* sps., and fungi such as *Aspergillis* sps., *Fusarium* sps., and *Trichophyton* sps.

In some embodiments, compositions of the present disclosure comprise a heme-haloperoxidase, and ethanolamine, diethanolamine, or propanolamine. In some embodiments, compositions of the present disclosure comprise a heme-haloperoxidase and ethanolamine. In some embodiments, compositions of the present disclosure comprise a heme-haloperoxidase and diethanolamine. In some embodiments, compositions of the present disclosure comprise a heme-haloperoxidase and propanolamine.

In some embodiments, the heme-haloperoxidase is selected from the group consisting of eosinophil peroxidase, myeloperoxidase, and lactoperoxidase. In some embodiments, the heme-haloperoxidase is myeloperoxidase. In some embodiments, the heme-haloperoxidase is lactoperoxidase. In some embodiments, the heme-haloperoxidase is eosinophil peroxidase.

As illustrated in the Examples, the addition of ethanolamine, diethanolamine, or propanolamine to a composition comprising a heme-haloperoxidase, e.g. eosinophil peroxidase, and a peroxide or peroxide-producing oxidase, in the presence of halide, enhances the microbicidal activity of the composition.

In some embodiments, a composition for killing or inhibiting the growth of pathogenic microorganisms comprises eosinophil peroxidase, a peroxide, and ethanolamine, wherein the ethanolamine enhances the microbicidal activity of the eosinophil peroxidase.

In some embodiments, a composition for killing or inhibiting the growth of pathogenic microorganisms comprises eosinophil peroxidase, a peroxide source, and ethanolamine, wherein the ethanolamine enhances the microbicidal activity of the eosinophil peroxidase.

In some embodiments, a composition for killing or inhibiting the growth of pathogenic microorganisms comprises eosinophil peroxidase, a peroxide, and diethanolamine, wherein the diethanolamine enhances the microbicidal activity of the eosinophil peroxidase.

In some embodiments, a composition for killing or inhibiting the growth of pathogenic microorganisms comprises eosinophil peroxidase, a peroxide source, and diethanolamine, wherein the diethanolamine enhances the microbicidal activity of the eosinophil peroxidase.

In some embodiments, a composition for killing or inhibiting the growth of pathogenic microorganisms comprises eosinophil peroxidase, a peroxide, and propanolamine, wherein the propanolamine enhances the microbicidal activity of the eosinophil peroxidase.

In some embodiments, a composition for killing or inhibiting the growth of pathogenic microorganisms comprises eosinophil peroxidase, a peroxide source, and propanolamine, wherein the propanolamine enhances the microbicidal activity of the eosinophil peroxidase.

In some embodiments, the compositions of the present disclosure comprise eosinophil peroxidase in a concentration of from about 5 µg/mL to about 100 µg/mL or greater. In some embodiments, the compositions of the present disclosure comprise eosinophil peroxidase in a concentration of from about 6.25 µg/mL to about 50 µg/mL. In some embodiments, the compositions of the present disclosure comprise eosinophil peroxidase in a concentration of 6.25 µg/mL, 12.5 µg/mL, 25 µg/mL, 50 µg/mL, or 100 µg/mL.

In some embodiments, the compositions of the present disclosure comprise ethanolamine, diethanolamine, or propanolamine in a concentration of from about 1 mM to about 20 mM or greater. In some embodiments, the compositions of the present disclosure comprise ethanolamine, diethanolamine, or propanolamine in a concentration of from about 1 mM to about 10 mM. In some embodiments, the compositions of the present disclosure comprise ethanolamine, diethanolamine, or propanolamine in a concentration of 1.25 mM, 2.5 mM, 3 mM, 5 mM, 10 mM, or 20 mM.

The microbicidal activity of the heme-haloperoxidase compositions of the present disclosure involves the reaction of peroxide and halide to form hypohalite (hypohalide), and the reaction of peroxide and hypohalite (hypohalide) to form singlet molecular oxygen. Therefore, the activity of the compositions of the present disclosure is dependent upon the presence, at the site of microbicidal activity, of a suitable peroxide and halide. In some situations, peroxide (e.g., hydrogen peroxide) may be present at the site of microbicidal activity due, for example, to the activity of naturally occurring flora, and sufficient amounts of halide may be present in the physiological milieu to act as a cofactor in the conversion reaction. In these situations, no additional peroxide or halide need be administered or included in the compositions of the present disclosure. In these situations, compositions of the present disclosure comprise a heme-haloperoxidase and ethanolamine, diethanolamine, or propanolamine. In some embodiments, compositions of the present disclosure comprise eosinophil peroxidase and ethanolamine. In some embodiments, compositions of the present disclosure comprise eosinophil peroxidase and diethanolamine. In some embodiments, compositions of the present disclosure comprise eosinophil peroxidase and propanolamine. In other situations, it may be necessary or desirable to additionally provide hydrogen peroxide and/or halide at the site of treatment. Accordingly, as further discussed below, the compositions of the present disclosure may additionally comprise, if desired, a peroxide or agent capable of producing peroxide in vivo or in vitro, and a halide.

In some embodiments, compositions of the present disclosure further comprise a halide such as bromide. In some embodiments, the compositions of the present disclosure comprise a halide in a concentration of from about 1 mM to about 20 mM or greater. In some embodiments, the compositions of the present disclosure comprise a halide in a concentration of from about 1 mM to about 10 mM. In some embodiments, the compositions of the present disclosure comprise a halide in a concentration of 1.25 mM, 2.5 mM, 3 mM, 5 mM, 10 mM, or 20 mM. In some embodiments the halide is sodium bromide. In some embodiments, the halide is potassium bromide.

In some embodiments, the compositions of the present disclosure further comprise a peroxide or peroxide source. Suitable peroxides include hydrogen peroxide and alkyl hydroperoxides of the formula: R—OOH, wherein R is hydrogen or a short chain alkyl group having from 1 to 3 carbon atoms, and inorganic peroxides, such as boroperoxide or ureaperoxide. The oxidant activity of the organic peroxides generally decreases with increasing R chain length, as follows: $R=H>>CH_3>CH_3CH_2>CH_3(CH_2)_2$.

In some embodiments, the compositions of the present disclosure comprise hydrogen peroxide in a concentration from about 0.5 mM to about 9 mM or greater. In some embodiments, the compositions of the present disclosure comprise hydrogen peroxide in a concentration of 0.5 mM, 0.89 mM, 1.1 mM, 2.2 mM, 4.4 mM, or 8.9 mM.

In one embodiment, a composition of the present disclosure comprises 100 µg/mL, eosinophil peroxidase, 20 mM sodium bromide, 20 mM ethanolamine, and 8.9 mM hydrogen peroxide.

In one embodiment, a composition of the present disclosure comprises 50 µg/mL eosinophil peroxidase, 10 mM sodium bromide, 10 mM ethanolamine, and 4.5 mM hydrogen peroxide.

In one embodiment, a composition of the present disclosure comprises 25 µg/mL eosinophil peroxidase, 5 mM sodium bromide, 5 mM ethanolamine, and 2.2 mM hydrogen peroxide.

In one embodiment, a composition of the present disclosure comprises 12.5 µg/mL eosinophil peroxidase, 2.5 mM sodium bromide, 2.50 mM ethanolamine, and 1.1 mM hydrogen peroxide.

In one embodiment, a composition of the present disclosure comprises 6.25 µg/mL eosinophil peroxidase, 1.25 mM sodium bromide, 1.25 mM ethanolamine, and 0.5 mM hydrogen peroxide.

In one embodiment, a composition of the present disclosure comprises 10 µg/mL, eosinophil peroxidase, 2 mM sodium bromide, 3 mM ethanolamine, and 0.89 mM hydrogen peroxide.

In one embodiment, a composition of the present disclosure comprises 10 µg/mL eosinophil peroxidase, 2 mM sodium bromide, 3 mM diethanolamine, and 0.89 mM hydrogen peroxide.

In one embodiment, a composition of the present disclosure comprises 50 µg/mL, eosinophil peroxidase, 20 mM sodium phosphate, 10 mM sodium bromide, 20 mM propanolamine, and 8.9 mM hydrogen peroxide.

In some embodiments, the compositions of the present disclosure comprise an agent capable of producing hydrogen peroxide as an alternative to hydrogen peroxide. In some embodiments, the agent is a peroxide-producing oxidase. Peroxide-producing oxidases produce hydrogen peroxide in the presence of a substrate. Suitable peroxide-producing oxidases include, for example, glucose oxidase, cholesterol oxidase, and galactose oxidase. In some embodiments, the peroxide-producing oxidase is glucose oxidase. For this embodiment, the substrate is glucose. In some embodiments, the composition comprises glucose oxidase in a concentration of from about 10 µg/mL to about 20 µg/mL or greater. In some embodiments, the compositions of the present disclosure comprise glucose oxidase in a concentration of 10 µg/mL or 20 µg/mL.

In one embodiment, a composition of the present disclosure comprises 20 µg/mL glucose oxidase, 40 µg/mL eosinophil peroxidase, 2 mM sodium bromide, and 2.5 mM ethanolamine.

In one embodiment, a composition of the present disclosure comprises 20 µg/mL glucose oxidase, 20 µg/mL eosinophil peroxidase, 2 mM sodium bromide, and 1.2 mM ethanolamine.

In one embodiment, a composition of the present disclosure comprises 20 µg/mL glucose oxidase, 10 µg/mL eosinophil peroxidase, 2 mM sodium bromide, and 0.6 mM ethanolamine.

In one embodiment, a composition of the present disclosure comprises 20 µg/mL glucose oxidase, 5 µg/mL eosinophil peroxidase, 2 mM sodium bromide, and 0.3 mM ethanolamine.

In other aspects of the present disclosure, methods for using the heme-haloperoxidase compositions of the present disclosure are provided.

In some embodiments, the present disclosure provides methods for killing or inhibiting the growth of pathogenic microorganisms. In some embodiments, the methods comprise contacting the microorganisms, in the presence of peroxide and halide, with a composition comprising a heme-haloperoxidase and ethanolamine, diethanolamine, or propanolamine.

In some embodiments, the heme-haloperoxidase is selected from the group consisting of eosinophil peroxidase, myeloperoxidase, and lactoperoxidase. In some embodiments, the heme-haloperoxidase is myeloperoxidase. In some embodiments, the heme-haloperoxidase is lactoperoxidase. In some embodiments, the heme-haloperoxidase is eosinophil peroxidase.

In some embodiments, the method comprises contacting the microorganisms, in the presence of halide, with a composition comprising a heme-haloperoxidase, hydrogen peroxide or a peroxide-producing source, and ethanolamine, diethanolamine, or propanolamine.

In some embodiments, the method comprises contacting the microorganisms, in the presence of bromide, with a composition comprising eosinophil peroxidase, hydrogen peroxide, and ethanolamine.

In some embodiments, the method comprises contacting the microorganisms, in the presence of bromide, with a composition comprising eosinophil peroxidase, hydrogen peroxide, and diethanolamine.

In some embodiments, the method comprises contacting the microorganisms, in the presence of bromide, with a composition comprising eosinophil peroxidase, hydrogen peroxide, and propanolamine.

In some embodiments, the method comprises contacting the microorganisms with a composition comprising eosinophil peroxidase, hydrogen peroxide, bromide, and ethanolamine, diethanolamine, or propanolamine.

In some embodiments, the method comprises contacting the microorganisms, in the presence of bromide, with a composition comprising eosinophil peroxidase, a peroxide-producing oxidase, and ethanolamine. In some embodiments, the peroxide-producing oxidase is glucose oxidase.

In some embodiments, the method comprises contacting the microorganisms, in the presence of bromide, with a composition comprising eosinophil peroxidase, a peroxide-producing oxidase, and diethanolamine. In some embodiments, the peroxide-producing oxidase is glucose oxidase.

In some embodiments, the method comprises contacting the microorganisms, in the presence of bromide, with a composition comprising eosinophil peroxidase, a peroxide-producing oxidase, and propanolamine. In some embodiments, the peroxide-producing oxidase is glucose oxidase.

In some embodiments, the method comprises contacting the microorganisms with a composition comprising eosinophil peroxidase, glucose oxidase, bromide, and ethanolamine, diethanolamine, or propanolamine.

In another embodiment, the present disclosure provides a method for treating an infection in a human or animal subject. The method comprises administering to the site of infection an effective amount of a composition of the present disclosure.

In some embodiments, the methods comprise administering to the site of infection, in the presence of peroxide and halide, a composition comprising a heme-haloperoxidase and ethanolamine, diethanolamine, or propanolamine.

In some embodiments, the heme-haloperoxidase is selected from the group consisting of eosinophil peroxidase, myeloperoxidase, and lactoperoxidase. In some embodiments, the heme-haloperoxidase is myeloperoxidase. In some embodiments, the heme-haloperoxidase is lactoperoxidase. In some embodiments, the heme-haloperoxidase is eosinophil peroxidase.

In some embodiments, the method comprises administering to the site of infection, in the presence of halide, a composition comprising a heme-haloperoxidase, hydrogen peroxide or a peroxide-producing source, and ethanolamine, diethanolamine, or propanolamine.

In some embodiments, the method comprises administering to the site of infection, in the presence of bromide, a composition comprising eosinophil peroxidase, hydrogen peroxide, and ethanolamine.

In some embodiments, the method comprises administering to the site of infection, in the presence of bromide, a composition comprising eosinophil peroxidase, hydrogen peroxide, and diethanolamine.

In seine embodiments, the method comprises administering to the site of infection, in the presence of bromide, a composition comprising eosinophil peroxidase, hydrogen peroxide, and propanolamine.

In some embodiments, the method comprises administering to the site of infection a composition comprising eosinophil peroxidase, hydrogen peroxide, bromide, and ethanolamine, diethanolamine, or propanolamine.

In some embodiments, the method comprises administering to the site of infection a composition comprising eosinophil peroxidase, hydrogen peroxide, bromide, and ethanolamine, In some embodiments, the method comprises administering to the site of infection a composition comprising eosinophil peroxidase, hydrogen peroxide, bromide, and diethanolamine.

In some embodiments, the method comprises administering to the site of infection a composition comprising eosinophil peroxidase, hydrogen peroxide, bromide, and propanolamine.

In some embodiments, the method comprises administering to the site of infection, in the presence of bromide, a composition comprising eosinophil peroxidase, a peroxide-producing oxidase, and ethanolamine. In some embodiments, the peroxide-producing oxidase is glucose oxidase.

In some embodiments, the method comprises administering to the site of infection, in the presence of bromide, a composition comprising eosinophil peroxidase, a peroxide-producing oxidase, and diethanolamine. In some embodiments, the peroxide-producing oxidase is glucose oxidase.

In some embodiments, the method comprises administering to the site of infection, in the presence of bromide, a composition comprising eosinophil peroxidase, a peroxide-producing oxidase, and propanolamine. In some embodiments, the peroxide-producing oxidase is glucose oxidase.

In some embodiments, the method comprises administering to the site of infection a composition comprising eosinophil peroxidase, glucose oxidase, bromide, and ethanolamine, diethanolamine, or propanolamine.

In some embodiments, the method comprises administering to the site of infection a composition comprising eosinophil peroxidase, glucose oxidase, bromide, and ethanolamine, In some embodiments, the method comprises administering to the site of infection a composition comprising eosinophil peroxidase, glucose oxidase, bromide, and diethanolamine.

In some embodiments, the method comprises administering to the site of infection a composition comprising eosinophil peroxidase, glucose oxidase, bromide, and propanolamine.

In the practice of methods of the present disclosure, for the heme-haloperoxidase compositions that include a peroxide-producing oxidase (e.g., glucose oxidase), the heme-haloperoxidase composition is preferably administered to the site to be treated separately from the administration of the composition that comprises the substrate for the oxidase (e.g., glucose). The sequence of administration is not critical; the heme-haloperoxidase composition can be administered before or after administration of the substrate composition.

The compositions and methods of the present disclosure are highly suitable for the topical treatment of microbial infections in a human or non-human mammalian subject at sites permitting direct contact of the compositions of the present disclosure with the microbial infection, such as, for example, infections of the skin, eyes, ears, mouth, nasal and sinus passages, traumatic injury sites, surgical sites and the like.

The compositions of the present disclosure are based on the use of dioxygenating heme-haloperoxidases, e.g. eosinophil peroxidase, which exhibit selective affinity for pathogenic microorganisms. Therefore, when the compositions of the present disclosure are used in human or animal subjects, high potency microbicidal action can be directed to the pathogenic microorganisms without associated host tissue destruction or disruption of normal flora; i.e., the antiseptic action is selective and confined to the pathogenic microorganisms.

As used herein, the term "normal flora" means bacteria, which normally reside in or on body surfaces of a healthy host at symbiotic levels. Normal flora include, for example, the lactic acid family of bacteria in the mouth, intestine, or vagina of human subjects, e.g., *Streptococcus* (viridans) in the mouth, and *Lactobacillus* sp. (e.g., Tissier's *bacillus* and Doderlein's *bacillus*) in the intestines of breast-fed infants, external genitalia, anterior urethra and vagina. Microorganisms which constitute normal flora of a host are well known (e.g., see *Principles and Practice of Infectious Diseases*, supra, New York, pp. 34-36 and 161). It has been found that heme-haloperoxidases, e.g. eosinophil peroxidase, selectively bind to many pathogenic bacteria and fungi in preference over normal flora. In in vivo applications, the host is preferably treated with an amount of compositions of the present disclosure which are ineffective to eliminate normal flora from the host.

The compositions and methods of the present disclosure are effective for treating polymicrobial as well as multidrug resistant infections. Polymicrobial diseases involve multiple infectious agents and are referred to as complex, complicated, mixed, dual, secondary, synergistic, concurrent, polymicrobial, or coinfections. Polymicrobial diseases include, for example, infections associated with abscesses, AIDS-related opportunistic infections, conjunctivitis, gastroenteritis, hepatitis, multiple sclerosis, otitis media, periodontal diseases, respiratory diseases, and genital infections. In addition, since the compositions of the present disclosure operate by an entire different mechanism of action than those involved in conventional antibiotic therapy, in some embodiments the compositions of the present disclosure are also highly useful in the treatment of infections caused, at least in part, by multidrug resistant pathogens, such as MRSA (methicillin-resistant *Staphylococcus aureus*), VRSA (Vancomycin-resistant *S. aureus*), VRE (Vancomycin-Resistant *Enterococcus*), Penicillin-Resistant *Enterococcus*, PRSP (Penicillin-resistant *Streptococcus pneumoniae*), isoniazid/rifampin-resistant *Mycobacterium tuberculosis* and other antibiotic-resistant strains of *E. coli, Salmonella, Campylobacter*, and Streptococci. Such bacteria are herein referred to as "antibiotic-resistant" or "drug-resistant" or "multidrug-resistant", or by other similar terms that are well understood in the art.

The compositions of the present disclosure may be administered alone or in combination with one or more other therapeutic agents. Representative additional therapeutic agents that may be used in combination with the compositions of the present disclosure include, for example, antibiotic or antiseptic agents such as anti-bacterial agents, anti-fungicides, anti-viral agents and/or anti-parasitic agents. In some embodiments, the additional therapeutic agents may be one or more penicillins, cephalosporins, carbacephems, cephamycins, carbapenems, monobactams, aminoglycosides, glycopeptides, quinolones, tetracyclines, macrolides, and/or fluoroquinolones. In some embodiments, the additional therapeutic agents may be iodine, silver, copper, chlorhexidine, polyhexanide, biguanides, chitosan and/or acetic acid. The one or more additional therapeutic agents of the present disclosure may be incorporated as part of the same composition or may be administered separately.

For in viva applications, the compositions of the present disclosure can be administered in any effective pharmaceutically acceptable form to warm blooded animals, including human and animal subjects (e.g., in topical, lavage, oral, vaginal or suppository dosage forms) as a topical, buccal, nasal spray, aerosol for inhalation or in any other manner effective to deliver active eosinophil peroxidase to a site of microorganism infection. The route of administration will preferably be designed to obtain direct contact of the antiseptic compositions with the infecting microorganisms.

In one aspect of the present disclosure, the compositions of the present disclosure are delivered or administered topically to areas of a human or animal subject that are susceptible to infection, such as, for example, to the gums, eyes, ears, skin, wounds, vaginal areas, groin areas, bed sores, burns, areas under medical dressings, diapers or other coverings which are likely to be moist, and the like.

In some embodiments, the compositions of the present disclosure additionally comprise pharmaceutically acceptable excipients, for example, aqueous or organic solvents, buffering agents, emulsifiers, gelling agents, moisturizers, stabilizers, surfactants, wetting agents, preservatives, time release agents, and minor amounts of humectants, sequestering agents, dyes, perfumes, and other components commonly employed in pharmaceutical compositions for topical administration. In some embodiments, in some embodiments, the compositions of the present disclosure further comprise phosphate buffered saline. In some embodiments, the compositions of the present disclosure further comprise polysorbate 80.

For topical applications, the pharmaceutically acceptable carrier may take the form of liquids, creams, foams, lotions, ointments, suspensions, suppositories or gels. In addition, the compositions of the present disclosure may be impregnated into absorptive materials, such as sutures, bandages, and gauze, or coated onto the surface of solid phase materials, such as staples, zippers and catheters to deliver the compositions to a site for the prevention of microbial infection. Other delivery systems of this type will be readily apparent to those skilled in the art.

In other embodiments, the present disclosure provides compositions and methods for inhibiting the growth of pathogenic microorganisms in vitro, particularly in applications where biomedical devices, such as bandages, surgical instruments, suturing devices, catheters, dental appliances, contact lenses and the like, require disinfection or sterilization and where the device is to be subsequently contacted with host tissue. Thus, high potency heme-haloperoxidase formulations of the present disclosure can serve as in vitro disinfecting or sterilizing preparations. By limiting the time period of hydrogen peroxide availability, heme-haloperoxidase formulations of the present disclosure can be made sufficiently potent to insure disinfection and even sterilization of a material or device before contact with host tissue.

Any potential toxicity to normal flora and host tissue associated with the use of these high potency formulations ceases when peroxide is depleted, and as such, the formulation-treated material or device can be brought in contact with host tissue without additional washing or detoxification.

In one aspect the heme-haloperoxidase compositions of the present disclosure may be constructed as a binary formulation in which the composition's active agents are formulated in two separate parts for consolidation at the time of use.

In some embodiments, the binary formulation comprises a first composition comprising a heme-haloperoxidase and ethanolamine, diethanolamine, or propanolamine in an aqueous medium and a second composition comprising a peroxide, for example hydrogen peroxide. In some embodiments, the first composition comprises eosinophil peroxidase and ethanolamine. In some embodiments, the first composition comprises eosinophil peroxidase and diethanolamine. In some embodiments, the first composition comprises eosinophil peroxidase and propanolamine. Either the first composition or the second composition, or both, may further comprise a halide. In some embodiments, the halide is sodium bromide. In some embodiments, the halide is potassium bromide.

In some embodiments, the binary formulation comprises a first composition comprising a heme-haloperoxidase, a peroxide-producing oxidase, and ethanolamine, diethanolamine, or propanolamine in an aqueous medium and a second composition comprising a substrate for the peroxide-producing oxidase in an aqueous medium. In some embodiments, the first composition comprises eosinophil peroxidase, a peroxide-producing oxidase, and ethanolamine. In some embodiments, the first composition comprises eosinophil peroxidase, a peroxide-producing oxidase, and diethanolamine. In some embodiments, the first composition comprises eosinophil peroxidase, peroxide-producing oxidase, and propanolamine. In some embodiments, the peroxide-producing oxidase is glucose oxidase and the substrate is glucose. Either the first composition or the second composition, or both, may further comprise a halide. In some embodiments, the halide is sodium bromide. In some embodiments, the halide is potassium bromide.

In some embodiments, in which a binary formulation of the present disclosure is used for sterilization of articles, and the first composition of the binary formulation comprises a peroxide-producing oxidase, the second composition, i.e. the substrate, may be provided, for example, in the form of a solid wafer. For sterilization of an article (e.g., a surgical instrument or a contact lens) the substrate wafer may be placed in a sterilization chamber along with the item to be sterilized. The first composition comprising a heme-haloperoxidase, a peroxide-producing oxidase, and ethanolamine, diethanolamine, or propanolamine are added to initiate sterilization. In some embodiments, the first composition may additionally comprise alcohol in order to facilitate substrate solubilization. This system will produce sustained microbicidal action as long as sufficient substrate is present to drive the reaction.

The following examples are provided for the purpose of illustrating, not limiting, the present disclosure. Because of issues related to the electronic reproduction of photographs of media plates showing the presence or absence of bacterial growth, the data from the experiments performed in the following examples are not shown.

EXAMPLES

Example 1

This example illustrates that the microbicidal activity of eosinophil peroxidase/ethanolamine compositions of the present disclosure is greater than the microbicidal activity of eosinophil peroxidase/amino acid compositions.

TABLE 1

Formulations A

| Component | Concentration | | | | |
|---|---|---|---|---|---|
| | Plate 1 | Plate 2 | Plate 3 | Plate 4 | Plate 5 |
| Glucose Oxidase (GO) | 20 ug/mL | 20 ug/mL | 20 ug/mL | 20 ug/mL | 20 ug/mL |
| Porcine eosinophil peroxidase (pEPO) | 40 ug/mL | 20 ug/mL | 10 ug/mL | 5 ug/mL | 2.5 ug/mL |
| Ethanolamine | 2.4 mM | 1.2 mM | 0.6 mM | 0.3 mM | 0.15 mM |

TABLE 2

Formulations B

| Component | Concentration | | | | |
|---|---|---|---|---|---|
| | Plate 1 | Plate 2 | Plate 3 | Plate 4 | Plate 5 |
| Glucose Oxidase (GO) | 20 ug/mL | 20 ug/mL | 20 ug/mL | 20 ug/mL | 20 ug/mL |
| Porcine eosinophil peroxidase (pEPO) | 40 ug/mL | 20 ug/mL | 10 ug/mL | 5 ug/mL | 2.5 ug/mL |
| L-alanine | 0.8 mM | 0.4 mM | 0.2 mM | 0.1 mM | 0.05 mM |
| L-proline | 0.8 mM | 0.4 mM | 0.2 mM | 0.1 mM | 0.05 mM |
| Glycine | 0.8 mM | 0.4 mM | 0.2 mM | 0.1 mM | 0.05 mM |

Formulations A and Formulations B were prepared by combining the components as indicated in Table 1 and Table 2, respectively, in PBS (phosphate buffered saline (pH 7.4) containing 2 mM NaBr and 1% (v:v) Tween-80 ("PBS+"). Each reaction was initiated by the addition of glucose (4.5% w/v, final concentration). One minute after initiation, Staphylococcus aureus ($10^9$ cfu*/mL, final concentration) (*colony forming units) was added and the reaction was incubated at room temperature for one minute. The reaction was stopped by adding 450 µL sterile PBS to 50 µL of each reaction formulation, and 0.1 mL of each reaction formulation was plated. The plates were incubated overnight at 36° C.

The control reaction was performed with a composition containing 20 µg glucose oxidase in PBS+(without eosinophil, amino acids, or ethanolamine.)

Microbicidal activity is evidenced by the amount of bacterial growth on the individual plates.

Results.

The data from the experiments performed in Example 1 illustrate that Formulation A, comprising pEPO and ethanolamine, was more effective at killing S. aureus bacteria than Formulation B, comprising pEPO and amino acids. A more effective kill is observed over the range of concentrations of pEPO and ethanolamine (compared to pEPO and amino acids), from high concentrations of pEPO (40 µg/mL) and ethanolamine (2.4 mM) to low concentrations of pEPO (2.5 µg/mL) and ethanolamine (0.15 mM). The superior microbicidal activity of formulations comprising pEPO and ethanolamine, compared to formulations comprising pEPO and amino acids, is particularly evident at lower concentrations of pEPO and ethanolamine. Formulations of pEPO/ethanolamine, showed no bacterial growth, compared to pEPO/amino acid formulations, all of which exhibited some bacterial growth.

Furthermore, on a weight-by-weight ratio, in the presence of ethanolamine, a concentration of pEPO that is one fourth that of glucose oxidase is sufficient to support a complete kill after a one-minute incubation period.

Example 2

This example illustrates that the microbicidal activity of pEPO is limited by the amount of glucose oxidase.

Example 3

This example illustrates that a composition comprising hydrogen peroxide, pEPO, and ethanolamine has microbicidal activity comparable to a composition comprising glucose, glucose oxidase, pEPO, and ethanolamine.

TABLE 4

Formulations D

| | Concentration | | |
|---|---|---|---|
| Component | Plate 1 | Plate 2 | Plate 3 |
| Glucose Oxidase (GO) | 20 ug/mL | 10 ug/mL | 5 ug/mL |
| Porcine eosinophil peroxidase (pEPO) | 20 ug/mL | 10 ug/mL | 5 ug/mL |
| Ethanolamine | 3 mM | 3 mM | 3 mM |

TABLE 5

Formulations E

| | Concentration | | |
|---|---|---|---|
| Component | Plate 4 | Plate 5 | Plate 6 |
| Hydrogen Peroxide ($H_2O_2$) | 0.89 mM | 0.89 mM | 0.89 mM |
| Porcine eosinophil peroxidase (pEPO) | 20 ug/mL | 10 ug/mL | 5 ug/mL |
| Ethanolamine | 3 mM | 3 mM | 3 mM |

Formulations D were prepared by combining glucose oxidase, pEPO, and ethanolamine as indicated in Table 4 in PBS+. Formulations E were prepared by combining hydrogen peroxide, pEPO, and ethanolamine as indicated in Table 5 in PBS+. Reactions were carried out as described in Example 1, except that glucose was only added to Formulations D.

Results.

The data from the experiments performed in Example 3 illustrate that the microbicidal activity of compositions comprising pEPO, ethanolamine, and hydrogen peroxide are comparable to the microbicidal activity of compositions

TABLE 3

Formulations C

| | Concentration | | | | | |
|---|---|---|---|---|---|---|
| Component | Plate 1 | Plate 2 | Plate 3 | Plate 4 | Plate 5 | Plate 6 |
| Glucose Oxidase (GO) | 20 ug/mL | 10 ug/mL | 5 ug/mL | 2.5 ug/mL | 1.25 ug/mL | 0.63 ug/mL |
| Porcine eosinophil peroxidase (pEPO) | 20 ug/mL | 10 ug/mL | 5 ug/mL | 2.5 ug/mL | 1.25 ug/mL | 0.63 ug/mL |
| Ethanolamine | 2.4 mM | 1.2 mM | 0.6 mM | 0.3 mM | 0.15 mM | 0.075 mM |

Formulations C were prepared by combining glucose oxidase and pEPO as indicated in Table 3 in PBS+. Reactions were carried out as described in Example 1.

Results.

The data from the experiments performed in Example 2, in conjunction with the data from the experiments performed in Example 1, illustrate that the microbicidal activity of pEPO is limited by the concentration of glucose oxidase.

comprising pEPO, ethanolamine, and glucose/glucose oxidase. Furthermore, concentrations of pEPO as low as 10 µg/mL are effective to result in a complete kill of the bacteria.

Example 4

This example illustrates that a composition comprising hydrogen peroxide and eosinophil peroxidase has increased microbicidal activity compared to neat hydrogen peroxide.

TABLE 6

Formulations F

| Component | Control | Plate 1 | Plate 2 | Plate 3 | Plate 4 | Plate 5 |
|---|---|---|---|---|---|---|
| | | | Concentration | | | |
| Hydrogen peroxide | 0.3% (89 mM) | 0.25 mM | 0.5 mM | 1.1 mM | 2.2 mM | 4.5 mM |
| Porcine eosinophil peroxidase | | 3.1 ug/mL | 6.25 ug/mL | 12.5 ug/mL | 25 ug/mL | 50 ug/mL |
| Ethanolamine | | 0.625 mM | 1.25 mM | 2.5 mM | 5 mM | 10 mM |
| Sodium Bromide | | 0.625 mM | 1.25 mM | 2.5 mM | 5 mM | 10 mM |

Formulations F were prepared by combining the components as indicated in Table 6 in PBS+1% Tween 80. *S. aureus* ($10^9$ cfu/mL, final concentration) was added and the reaction was incubated at room temperature for one minute. The reaction was stopped by plating. The plates were incubated overnight at 36° C.

Results.

The data from the experiments performed in Example 4 illustrate that concentrations of pEPO and $H_2O_2$ as low as 6.25 ug/mL and 0.5 mM, respectively, are effective to result in a complete kill of the bacteria after one minute of reaction time. Furthermore, the data illustrate that the addition of eosinophil peroxidase to a solution of hydrogen peroxide enhances the microbicidal activity of hydrogen peroxide. For example, it was found that neat hydrogen peroxide at a high concentration of 89 mM is ineffective in killing the bacteria, whereas, with the addition of pEPO, a hydrogen peroxide concentration of as low as 0.5 mM achieves a 100% kill of the bacteria.

Example 5

The reactions described in Example 4 were repeated with Formulations F for plates 2-5 with the added condition that the formulations were incubated (aged) 1 or 30 minutes prior to adding the *S. aureus* bacteria. The reaction was incubated at room temperature for one minute after the addition of bacteria. An additional sample was added (100 μg/mL pEPO; 8.9 mM $H_2O_2$; 20 mM ethanolamine; and 20 mmM NaBr). The data from the experiments performed in Example 5 illustrate that a composition of pEPO and $H_2O_2$ retains its microbicidal activity for at least up to thirty minutes.

Example 6

This example illustrates that ethanolamine enhances the microbicidal activity of compositions comprising pEPO and $H_2O_2$.

TABLE 7

Formulations G

| Component | Plate 1 | Plate 2 | Plate 3 | Plate 4 | Plate 5 | Plate 6 |
|---|---|---|---|---|---|---|
| | | | Concentration | | | |
| Hydrogen peroxide | 0.25 mM | 0.5 mM | 1.1 mM | 2.2 mM | 4.5 mM | 8.9 mM |
| Porcine eosinophil peroxidase | 3.1 ug/mL | 6.25 ug/mL | 12.5 ug/mL | 25 ug/mL | 50 ug/mL | 100 ug/mL |
| Sodium Bromide | 0.625 mM | 1.25 mM | 2.5 mM | 5 mM | 10 mM | 20 mM |

Formulations G were prepared by combining the components as indicated in Table 7 in PBS+1% Tween 80. The reactions were carried out as described in Example 5.

Results.

The data from the experiments performed in Example 6 illustrate that pEPO/$H_2O_2$ compositions have relatively little microbicidal activity without the presence of ethanolamine. When the results from Example 6 are compared to the results from Example 5, it can be seen that ethanolamine significantly enhances the microbicidal activity of pEPO/$H_2O_2$ compositions.

Example 7

This example illustrates that ethanolamine or diethanolamine added to compositions comprising pEPO increases the amount of time such formulations retain microbicidal activity.

TABLE 8

Formulations H

| Component | Concentration | | | | |
|---|---|---|---|---|---|
| | Plate 1 | Plate 2 | Plate 3 | Plate 4 | Plate 5 |
| Porcine eosinophil peroxidase (pEPO) | 10 ug/mL | 10 ug/mL | 10 ug/mL | 10 ug/mL | 10 ug/mL |
| Ethanolamine | | 3 mM | | | |
| Diethanolamine | | | 3 mM | | |
| Triethanolamine | | | | 3 mM | |
| L-serine | | | | | 3 mM |

Formulations H were prepared by combining the components as indicated in Table 8 in PBS+1% Tween 80+2 mM NaBr. Two sets of reactions were carried out with Formulations H, as indicated below.

Reaction 1.

S. aureus at $10^8$ cfu/mL, (final concentration) was added to each of the Formulations H. The mixture was incubated for 5 minutes at room temperature. The reaction was initiated by adding hydrogen peroxide at a final concentration of 0.89 mM to each reaction mixture. The reaction was incubated for one minute at room temperature and then stopped by plating the reaction mixture. The plates were incubated overnight at 36° C.

Reaction 2.

Hydrogen peroxide (at final concentration of 0.89 mM) was added to each of Formulations H. The reaction mixture was incubated for 5 minutes at room temperature. The reaction was initiated by adding S. aureus at $10^8$ cfu/mL (final concentration) to each reaction mixture. The reaction was incubated for one minute at room temperature and then stopped by plating the reaction mixture. The plates were incubated overnight at 36° C.

Results.

In Reaction 1, the S. aureus bacteria is incubated with pEPO for 5 minutes before the addition of $H_2O_2$, and therefore, Reaction 1 is "aged" (in the presence of $H_2O_2$) for 0 minutes. In Reaction 2, the $H_2O_2$ is incubated with the pEPO for 5 minutes before the S. aureus bacteria is added, and thus Reaction 2 is "aged" for 5 minutes.

The data from the experiments performed in Example 7 illustrate that pEPO alone, and in combination with ethanolamine, diethanolamine, and serine, exhibit some microbicidal activity after incubation for one minute with $H_2O_2$. In sharp contrast, pEPO in combination with triethanolamine (Plate 1) shows no microbicidal activity. Because pEPO alone (no additive) showed some bioactivity, the results from pEPO plus triethanolamine)-indicates that triethanolamine is inhibitory.

The data from the experiments performed in Example 7 also illustrate that when formulations comprising pEPO alone, and in combination with ethanolamine, diethanolamine, triethanolamine, or serine are incubated for 5 minutes with $H_2O_2$, only formulations comprising pEPO and ethanolamine or diethanolamine maintained microbicidal activity.

Example 8

This example illustrates that compositions comprising pEPO and ethanolamine or propanolamine retain microbicidal activity up to at least ninety-six hours

TABLE 9

Formulations I

| Component | Concentration | |
|---|---|---|
| | Plate 1 | Plate 2 |
| Porcine eosinophil peroxidase (pEPO) | 50 ug/mL | 50 ug/mL |
| Ethanolamine | 20 mM | |
| Propanolamine | | 20 mM |

Formulations I were prepared by combining the components as indicated in Table 9 in PBS+0.1% Tween 80+20 mM $NaPO_4$, 150 mM NaCl, 10 mM NaBr. Three sets of reactions were carried out with Formulations I, as indicated below.

Reaction 1.

The reactions were initiated by adding hydrogen peroxide at a final concentration of 8.9 mM to each of the Formulations 1. The reactions were incubated at room temperature for two minutes. S. aureus at $10^8$ cfu/mL (final concentration) was then added to each of the reaction mixtures. The reaction was incubated for one minute at room temperature and then stopped by plating the reaction mixture. Plates were developed overnight at 36° C.

Reaction 2.

The conditions for Reaction 2 were the same as for Reaction 1, except that the reactions were incubated for twenty-four hours at room temperature before addition of the S. aureus bacteria.

Reaction 3.

The conditions for Reaction 3 were the same as for Reaction 1, except that the reactions were incubated for ninety-six hours at room temperature before addition of the S. aureus bacteria.

The data from the experiments performed in Example 8 illustrate that compositions of the present disclosure comprising eosinophil peroxidase, halide, hydrogen peroxide, and ethanolamine or propanolamine retain microbicidal activity up to at least ninety-six hours, as evidenced by the complete kill of the microbes added to the formulations that were aged for up to ninety-six hours before the addition of bacteria.

Example 9

This example illustrates that compositions comprising eosinophil peroxidase and glycinamide or glycine methyl ester lose microbicidal activity over time; whereas compositions comprising eosinophil peroxidase and ethanolamine retain microbicidal activity for at least 24 hours.

TABLE 10

Formulations J

| Component | Concentration | | |
|---|---|---|---|
| | Plate 1 | Plate 2 | Plate 3 |
| Porcine eosinophil peroxidase (pEPO) | 50 ug/mL | 50 ug/mL | 50 ug/mL |
| Ethanolamine | 20 mM | | |
| Glycinamide | | 20 mM | |
| Glycine methyl ester | | | 20 mM |

Formulations I were prepared by combining the components as indicated in Table 9 in PBS+0.1% Tween 80+20 mM NaPO$_4$, 150 mM NaCl, 10 mM NaBr. Two sets of reactions were carried out with Formulations J, as indicated below.

Reaction 1.

The reactions were initiated by adding hydrogen peroxide at a final concentration of 8.9 mM to each of the Formulations J. The reactions were incubated at room temperature for two minutes before adding microbe. S. aureus at $10^8$ cfu/mL (final concentration) was then added to each of the reaction mixtures. The reaction was incubated for one minute at room temperature and then stopped by plating the reaction mixture. Plates were incubated overnight at 36° C.

Reaction 2.

The conditions for Reaction 2 were the same as for Reaction 1, except that the reactions were incubated for twenty-four hours at room temperature before addition of the S. aureus bacteria.

The data from the experiments performed in Example 9 illustrate that compositions comprising eosinophil peroxidase, halide, hydrogen peroxide, and glycinamide or glycine methyl ester show initial microbicidal activity. However, the data also illustrates that compositions comprising eosinophil peroxidase, halide, hydrogen peroxide, and glycinamide or glycine methyl ester lose microbicidal activity after twenty-four hours.

These results are in sharp contrast to the data from the experiments performed in Example 9 for compositions of the present disclosure comprising eosinophil peroxidase, halide, hydrogen peroxide, and ethanolamine, which retain microbicidal activity for twenty-four hours, and to the data from the experiments performed in Example 8, which show that compositions of the present disclosure comprising eosinophil peroxidase, halide, hydrogen peroxide, and ethanolamine or propanolamine retain microbicidal activity for at least up to ninety-six hours.

Summary.

The data in the above examples illustrate that the compositions of the present disclosure, comprising eosinophil peroxidase, hydrogen peroxide or a source of hydrogen peroxide, and ethanolamine, diethanolamine, or propanolamine, are more effective at killing bacteria than compositions comprising hydrogen peroxide alone; or hydrogen peroxide in combination with eosinophil peroxidase. The data also shows that compositions comprising eosinophil peroxidase and ethanolamine, diethanolamine, or propanolamine have superior microbicidal activity compared to compositions comprising eosinophil peroxidase and amino acids, or glycinamide, or glycine methyl ester.

The data in the examples further illustrate that compositions of the present disclosure comprising eosinophil peroxidase, hydrogen peroxide, and ethanolamine, diethanolamine, or propanolamine retain microbicidal activity over a period of time.

The concentrations of the various components described herein are for illustrative purposes only. The concentrations of the various components in the compositions of the present disclosure may vary widely depending on the conditions under which the compositions are employed, the environment of use and the desired result.

While the preferred embodiment of the present disclosure has been illustrated and described, it will be appreciated that various changes can be made therein without departing from the spirit and scope of the present disclosure.

The embodiments of the present disclosure in which an exclusive property or privilege is claimed are defined as follows:

1. A composition for killing or inhibiting the growth of pathogenic microorganisms, comprising: a mammalian eosinophil peroxidase, a peroxide or a peroxide source, and an amino alcohol selected from the group consisting of ethanolamine, diethanolamine, and propanolamine.

2. The composition of claim 1, wherein the amino alcohol enhances the microbicidal activity of the eosinophil peroxidase.

3. The composition of claim 1, wherein the peroxide is hydrogen peroxide.

4. The composition of claim 1, wherein the peroxide source is a peroxide-producing oxidase.

5. The composition of claim 4, wherein the peroxide-producing oxidase is glucose oxidase.

6. The composition of claim 1, wherein the amino alcohol is ethanolamine.

7. The composition of claim 1, wherein the amino alcohol is diethanolamine.

8. The composition of claim 1, wherein the amino alcohol is propanolamine.

9. The composition of claim 1, further comprising a halide.

10. The composition of claim 9, wherein the halide is bromide.

11. A composition for killing or inhibiting the growth of pathogenic microorganisms, comprising: a mammalian eosinophil peroxidase; a peroxide or a peroxide source; a halide; and an amino alcohol selected from the group consisting of ethanolamine, diethanolamine, and propanolamine, wherein the amino alcohol enhances the microbicidal activity of the eosinophil peroxidase.

12. The composition of claim 11, wherein the peroxide is hydrogen peroxide.

13. The composition of claim 11, wherein the peroxide source is a peroxide-producing oxidase.

14. The composition of claim 13, wherein the peroxide-producing oxidase is glucose oxidase.

15. The composition of claim 11, wherein the halide is bromide.

16. A method for killing or inhibiting the growth of pathogenic microorganisms, comprising: contacting the microorganisms, in the presence of a peroxide and a halide, with an effective amount of a composition comprising: a mammalian eosinophil peroxidase and an amino alcohol selected from the group consisting of ethanolamine, diethanolamine, and propanolamine.

17. The method of claim 16, wherein the peroxide is hydrogen peroxide.

18. The method of claim 16, wherein the halide is bromide.

19. A method of treating a microbial infection in a human or animal subject, comprising: administering to the site of infection, in the presence of a peroxide and a halide, an effective amount of a composition comprising: a mammalian eosinophil peroxidase and an amino alcohol selected from the group consisting of ethanolamine, diethanolamine, and propanolamine.

20. The method of claim 19, wherein the peroxide is hydrogen peroxide.

21. The method of claim 19, wherein the halide is bromide.

22. A binary formulation for killing or inhibiting the growth of pathogenic microorganisms comprising:
    (a) a first composition comprising a mammalian eosinophil peroxidase, and an amino alcohol selected from the group consisting of ethanolamine, diethanolamine, and propanolamine; and
    (b) a second composition comprising a peroxide, wherein the binary formulation is effective for killing or inhibiting the growth of the pathogenic microorganisms when the first composition and the second composition are combined in a single solution and come in contact with the pathogenic microorganisms.

23. The binary formulation of claim 22, wherein the peroxide is hydrogen peroxide.

24. The binary formulation of claim 22, wherein the first composition, the second composition, or both the first composition and the second composition, further comprise a halide.

25. The binary formulation of claim 24, wherein the halide is bromide.

26. A binary formulation comprising:
    (a) a first composition comprising a mammalian eosinophil peroxidase, a peroxide-producing oxidase, and an amino alcohol selected from the group consisting of ethanolamine, diethanolamine, and propanolamine; and
    (b) a second composition comprising a substrate for the peroxide-producing oxidase, wherein the binary formulation is effective for killing or inhibiting the growth of the pathogenic microorganisms when the first composition and the second composition are combined in a single solution and come in contact with the pathogenic microorganisms.

27. The binary formulation of claim 26, wherein the peroxide-producing oxidase is glucose oxidase and the substrate is glucose.

28. The binary formulation of claim 26, wherein the first composition, the second composition, or both the first composition and the second composition, further comprise a halide.

29. The binary formulation of claim 28, wherein the halide is bromide.

30. A binary formulation comprising:
    (a) a first composition comprising a mammalian eosinophil peroxidase, a peroxide-producing oxidase, and an amino alcohol selected from the group consisting of ethanolamine, diethanolamine, and propanolamine; and
    (b) a second composition comprising a substrate for the peroxide-producing oxidase, wherein the binary formulation is effective for killing or inhibiting the growth of the pathogenic microorganisms when the first composition and the second composition are each in solution form and are applied concurrently to the pathogenic microorganisms.

31. The binary formulation of claim 30, wherein the peroxide-producing oxidase is glucose oxidase and the substrate is glucose.

32. A binary formulation comprising:
    (a) a first composition comprising a mammalian eosinophil peroxidase, a peroxide-producing oxidase, and an amino alcohol selected from the group consisting of ethanolamine, diethanolamine, and propanolamine; and
    (b) a second composition comprising a substrate for the peroxide-producing oxidase, wherein the binary formulation is effective for killing or inhibiting the growth of the pathogenic microorganisms when the first composition and the second composition are each in solution form and are applied sequentially to the pathogenic microorganisms.

33. The binary formulation of claim 32, wherein the peroxide-producing oxidase is glucose oxidase and the substrate is glucose.

* * * * *